United States Patent [19]
Beyar et al.

[11] Patent Number: 5,782,838
[45] Date of Patent: Jul. 21, 1998

[54] CYTOSCOPE DELIVERY SYSTEM

[75] Inventors: Mordechay Beyar, Tel Aviv; Oren Globerman, Holon, both of Israel

[73] Assignee: Medtronic InStent, Inc., Eden Prairie, Minn.

[21] Appl. No.: 843,793

[22] Filed: Apr. 21, 1997

Related U.S. Application Data

[63] Continuation of Ser. No. 326,607, Oct. 20, 1994, abandoned.

[51] Int. Cl.$^6$ .................................................... A61F 11/00
[52] U.S. Cl. ............................................................. 606/108
[58] Field of Search ..................................... 606/108, 192, 606/191, 198, 194; 604/96

[56] References Cited

U.S. PATENT DOCUMENTS

| | | |
|---|---|---|
| 4,334,327 | 6/1982 | Lyman et al. . |
| 4,503,569 | 3/1985 | Dotter . |
| 4,655,771 | 4/1987 | Wallsten . |
| 4,768,507 | 9/1988 | Fischell . |
| 4,776,337 | 10/1988 | Palmaz . |
| 4,795,458 | 1/1989 | Regan . |
| 4,856,516 | 8/1989 | Hillstead . |
| 4,878,906 | 11/1989 | Lindemann et al. . |
| 4,886,062 | 12/1989 | Wiktor . |
| 4,913,141 | 4/1990 | Hillstead ................. 606/108 |
| 4,950,227 | 8/1990 | Savin et al. . |
| 4,969,458 | 11/1990 | Wiktor . |
| 4,990,155 | 2/1991 | Wilkoff . |
| 4,994,066 | 2/1991 | Voss ........................ 606/191 |
| 5,007,926 | 4/1991 | Derbyshire . |
| 5,019,085 | 5/1991 | Hillstead ................. 606/108 |
| 5,019,090 | 5/1991 | Pinchuk . |
| 5,026,377 | 6/1991 | Burton et al. . |
| 5,037,392 | 8/1991 | Hillstead et al. . |
| 5,037,427 | 8/1991 | Harada et al. . |
| 5,089,005 | 2/1992 | Harada . |
| 5,100,429 | 3/1992 | Sinofsky et al. . |
| 5,108,416 | 4/1992 | Ryan et al. . |
| 5,123,917 | 6/1992 | Lee . |
| 5,133,732 | 7/1992 | Wiktor . |
| 5,135,536 | 8/1992 | Hillstead . |
| 5,147,370 | 9/1992 | McNamara et al. . |
| 5,147,385 | 9/1992 | Beck et al. . |
| 5,158,548 | 10/1992 | Lau et al. . |
| 5,159,920 | 11/1992 | Condon et al. ............... 606/108 |
| 5,160,341 | 11/1992 | Brenneman et al. . |
| 5,167,614 | 12/1992 | Tessmann et al. . |
| 5,195,984 | 3/1993 | Schatz . |
| 5,201,757 | 4/1993 | Heyn et al. . |
| 5,242,399 | 9/1993 | Lau et al. . |
| 5,246,445 | 9/1993 | Yachia et al. ............... 606/108 |
| 5,411,507 | 5/1995 | Heckele ...................... 606/108 |

*Primary Examiner*—Gary Jackson
*Assistant Examiner*—Kevin Truong
*Attorney, Agent, or Firm*—Cowan, Liebowitz & Latman, P.C.

[57] ABSTRACT

This invention concerns a cystoscope delivery system for implanting a flexible, generally cylindrical, expandable stent. The system comprises a rigid or flexible sheath having distal and proximal ends, the sheath defining a central lumen and at least one secondary lumen extending therethrough and having two longitudinally displaced openings extending from a secondary lumen radially to the surface of the sheath, a rigid cystoscope comprising a distal scope member and a proximal viewing head, the distal scope member extending distally through the central lumen, a flexible, expandable stent having discrete proximal and distal ends, the stent being positioned circumferentially around the sheath, at least one release wire positioned in and extending through the secondary lumen or lumens, and two or three restraining members, two of which are positioned at respective ends of the stent and each having a restraining member extending over a respective end of the stent, the release wire or wires extending through at least one of said openings to hold one or both ends of the stent and thus to hold the stent in position, such that when the release wire or wires are pulled proximally, one or both ends of the stent are released from the restraining members to permit the stent to expand.

17 Claims, 4 Drawing Sheets

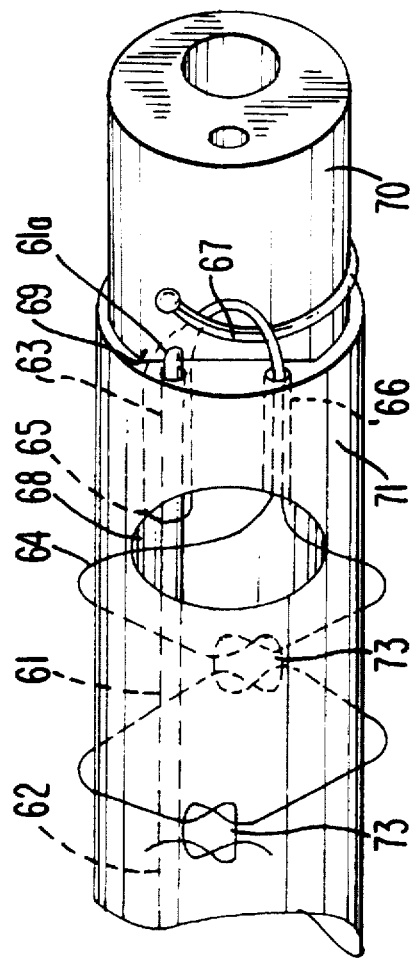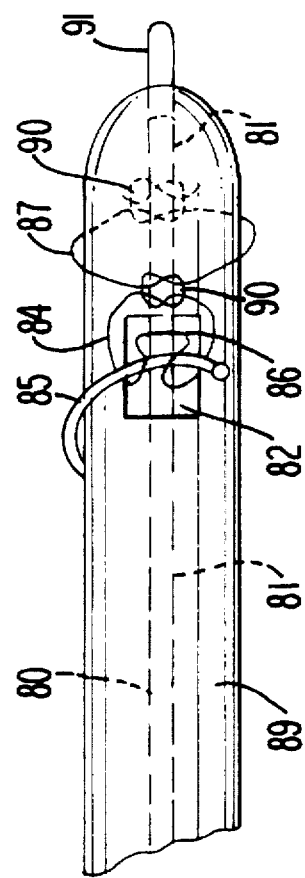

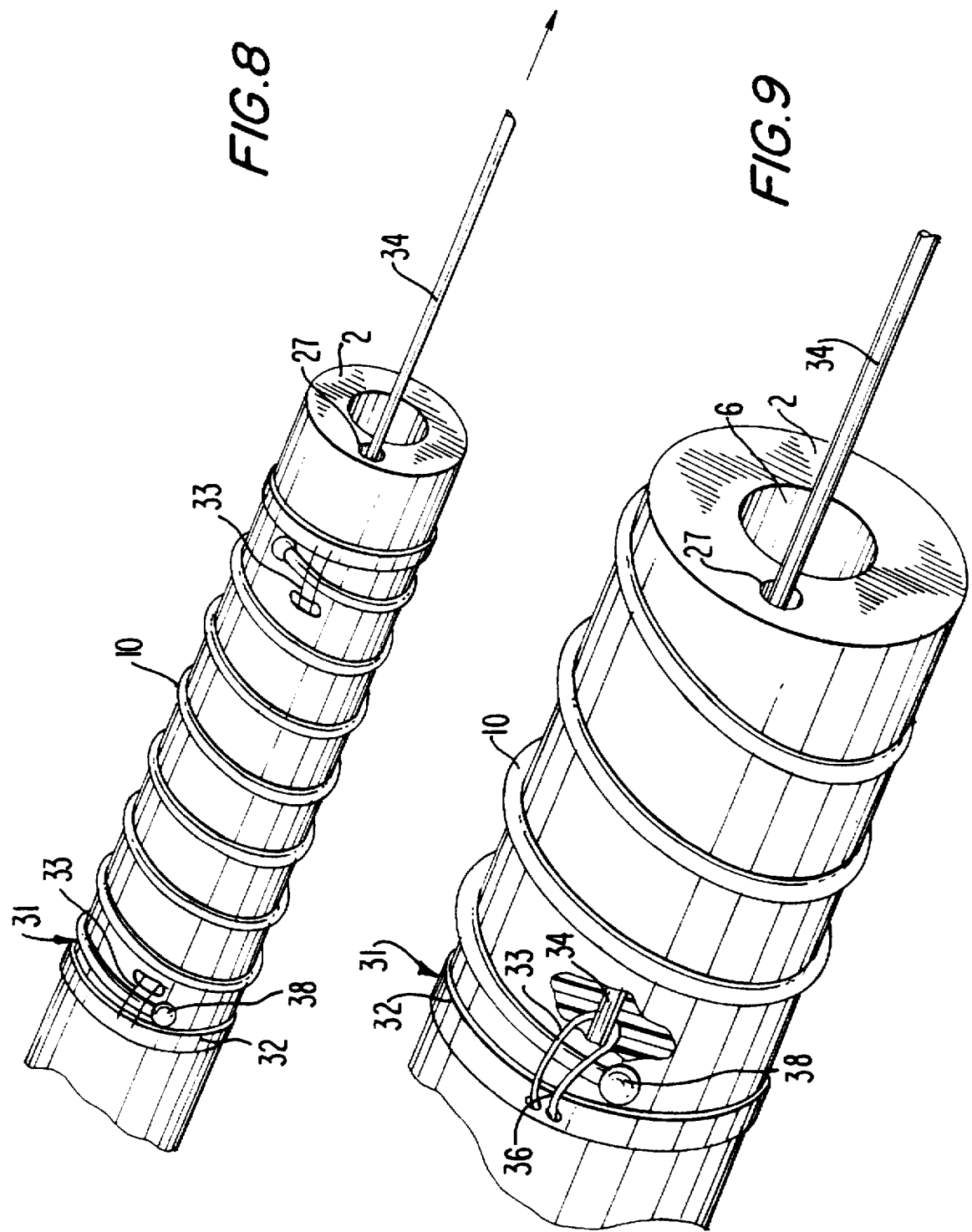

CYTOSCOPE DELIVERY SYSTEM

This application is a continuation, of application Ser. No. 08/326,607, filed Oct. 20, 1994, now abandoned.

FIELD OF THE INVENTION

This invention is directed to a stent delivery system. More particularly, this invention is directed to a stent delivery system wherein a metallic, polymeric, or bioabsorbable/biodegradable stent is delivered to a desired site on the distal end of a cystoscope sheath.

BACKGROUND OF THE INVENTION

It is well known that stents can be inserted into various corporal ducts for the purpose of enlarging said ducts or maintaining the size of said ducts. There are numerous patents in this area, including U.S. Pats. Nos. 4,334,327, 4,503,569, 4,655,771, 4,856,516, 4,969,458, 4,994,066, 5,007,926, 5,019,090, 5,123,917, 5,133,732, 5,135,536, 5,167,614, and 5,236,446. Such stents are usually delivered by flexible delivery means. See, for example, U.S. Pats. Nos. 4,768,507, 4,776,337, 4,795,458, 4,878,906, 4,886,062, 4,913,141, 4,950,227, 4,990,155, 5,026,377, 5,037,392, 5,037,427, 5,089,005, 5,100,429, 5,108,416, 5,147,370, 5,147,385, 5,158,548, 5,195,984, and 5,242,399. However, delivery or insertion by rigid delivery systems is disclosed in U.S. Pats. Nos. 5,160,341 and 5,201,757. All of the aforementioned patents are incorporated by reference.

While the above-described delivery systems do deliver the stents, that is the primary function. Such flexible systems may sometimes have a lumen or channel capable of another function.

OBJECTS OF THE INVENTION

It is an object of the invention to provide a novel stent delivery system for a self-expandable metallic or polymeric stent as well as for a bioabsorbable/biodegradable stent.

It is a further object of the invention to provide a stent delivery system where a rigid scope sheath acts as a stent delivery vehicle, into which rigid optics can be inserted.

It is yet a further object of the invention to provide a system which holds an expandable stent constrained on the delivery catheter and a system which releases an expandable stent gradually or instantly from the delivery catheter.

These and other objects of the invention will become more apparent from the discussion below.

BRIEF DESCRIPTION OF THE DRAWINGS

FIG. 6 and 7 are each a partial oblique view of a restraining means useful according to the invention; and FIGS. 8 and 9 are each an oblique, partial crosssectional close-up of the distal end of the embodiment shown in FIGS. 1 and 2.

DETAILED DESCRIPTION OF THE INVENTION

Applicant's invention is directed to a cystoscopic system for inserting a metallic, polymeric, or bioabsorbable/biodegradable stent into the urethral path as well as into other body ducts, such as esophageal, intestinal, and biliary ducts. The invention comprises cystoscopic scope sheath having a stent wound about its distal portion. More particularly, the cystoscopic stent delivery system of the invention comprises cystoscopic sheath member having distal and proximal ends and a cylindrical stent in a wound or prewound condition removably attached to the outer surface of the cystoscopic sheath member. The sheath can be rigid or sufficiently flexible to receive a flexible optics or cystoscope or a flexible endoscope. The lumen inside the cystoscopic sheath enables the insertion of a rigid scope through its lumen as well as irrigation with water or other fluids. When the stent is released, it expands in the radial direction to regain its larger original diameter.

The invention is also directed to a rotational relative movement delivery system in which a second tube is mounted on a cystoscope sheath and/or a rigid or flexible stent delivery catheter. The respective ends of the stent are each secured to one of the two tubes. Rotation of the tubes relative to one another permits control of stent constriction and reduction in diameter.

Figure 1:
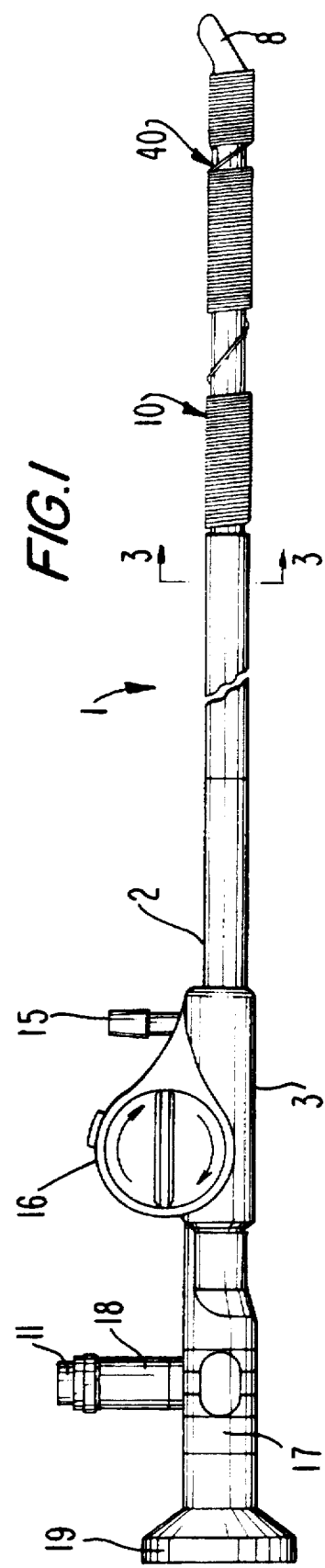
FIG. 1 is a plan view of an embodiment of the invention.
Figure 2:
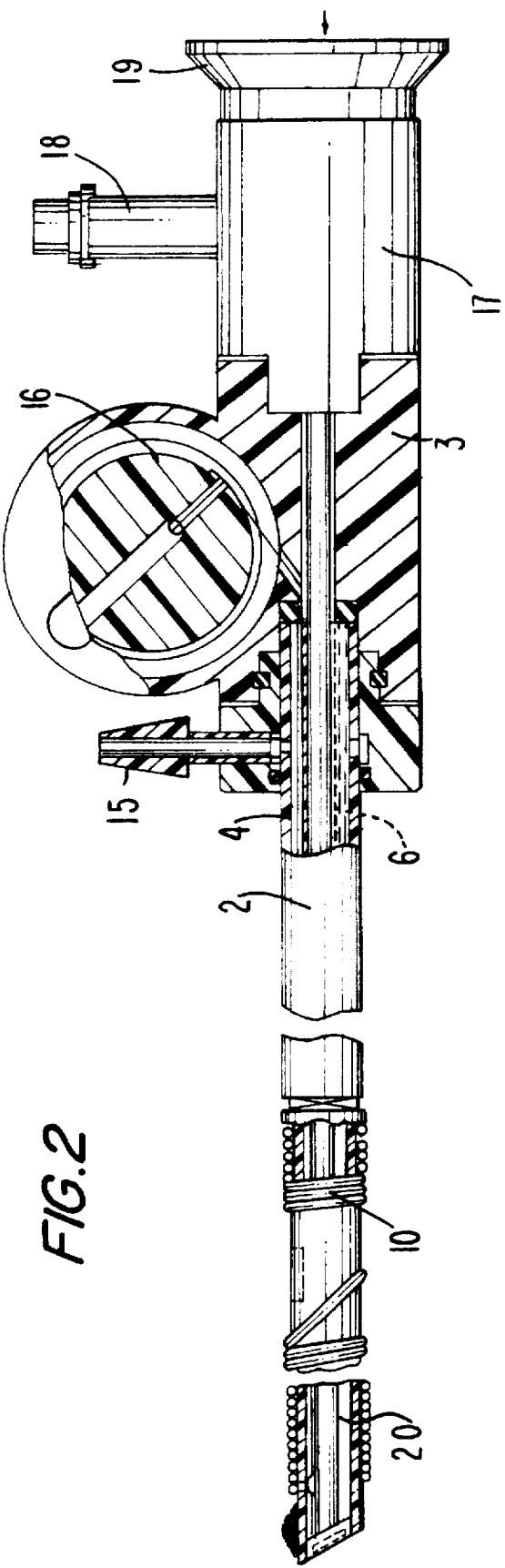
FIG. 2 is a partial cross-sectional view of the embodiment shown in FIG. 1.

The invention can perhaps be better appreciated from the drawings. As shown in FIGS. 1 and 2, the delivery system 1 comprises an elongated rigid or flexible sheath member 2 defining a central lumen 6 and a head 3. Sheath member 2 comprises at least one lumen 4 for one or more release wires 5 or water irrigation, and fiber optics for light and viewing in scope 20 extend distally through central lumen 6.

Stent 10 is positioned at or adjacent to the distal end 8 of sheath member 2.

Figure 3:
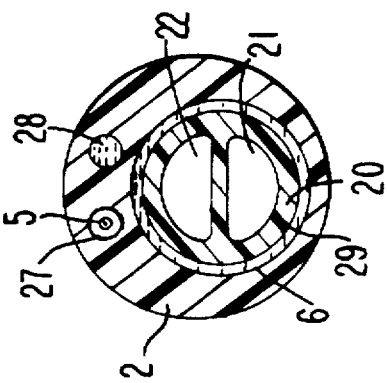
FIG. 3 is a perpendicular cross-sectional view of the embodiment shown in FIGS. 1 and 2.
Figure 4:
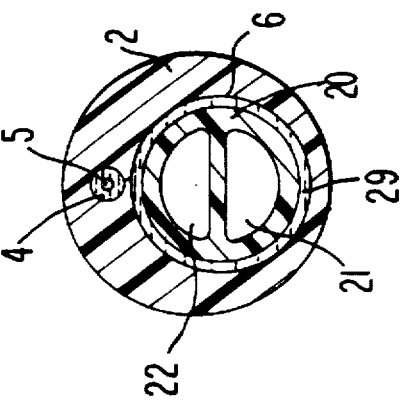
FIG. 4 is a perpendicular cross-sectional view of another embodiment of the invention.

Head 3 comprises fluid inlet 15 and release wire control 16. Cystoscope 17 comprises light input 18, viewing lens 19, and scope 20. Light input 18 comprises a suitable coupling 11 to a conventional coherent light source (not shown). The coherent light travels from said light source through said input 18 distally through a fiber optic bundle 21, such as is shown in FIGS. 3 and 4. An image is viewed through viewing optic 22 which extends proximally to viewing lens 19. Optionally viewing lens 19 could be optically connected to a remote viewing system (not shown), or the distal end of scope 20 may have a CCD chip in communication with a remote viewing means (not shown). A window 40 in between the stent length enables accurate placement of the stent in a desired place, such as in the intersphincteric or other area of the urethra or the bladder neck.

In FIG. 3, rigid member 2 is shown as having a single lumen 4 through which water or other fluid such as contrast fluid or air from fluid inlet 15 can travel distally for irrigation or one or more release wires 15 may extend. However, sheath member 2 may optionally comprise additional lumens, such as is shown in FIG. 4, where there is a release wire lumen 27, a fluid lumen 28, and a central lumen 6 for scope 20. Also, water or another fluid may be irrigated through central lumen 6, where it will move distally in the space 29 between the outer surface of the scope and the inner surface of central lumen 6. the embodiment of the invention shown in FIG. 5, the delivery system comprises an inner rigid or flexible tube 50, outer rigid or flexible tube 51, and stent 52, the proximal and distal ends of which are removably secured on the respective distal ends of tubes 50,51. Outer tube 51 does not extend distally as far as inner tube 50, to leave room for stent 52. The proximal end of outer tube 51 terminates in rotation member 53, which is longitudinally constrained but can rotate outer tube 51 relative to inner tube 50. For example, rotation member 53 may have an annular groove 54 which cooperates with annular projection 55.

Figure 5:
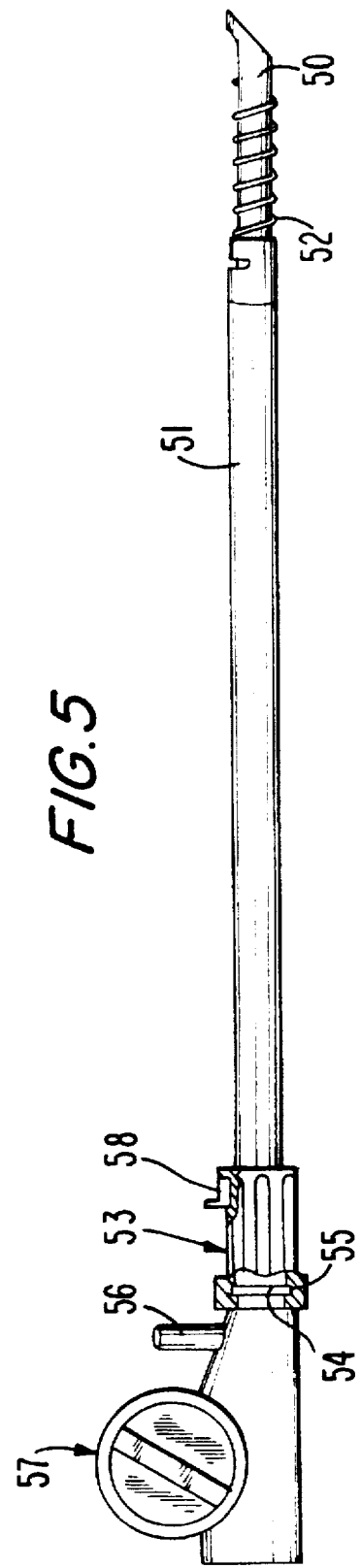
FIG. 5 is a plan view of another embodiment of the invention.

The embodiment of FIG. 5 is otherwise similar to the embodiment shown in FIGS. 1 to 4. This embodiment has a central lumen for receiving a cystoscope, fluid irrigation, or merely a guidewire, and one or more secondary lumens for receiving release wires or water through fluid inlet 56. Preferably outer tube 51 has one secondary lumen for a release wire and inner tube 50 has one or more secondary lumens. Rotation member 53 has a release member 58 for releasing the release wire engaged with the proximal end of stent 52, and release handle 57 releases the release wire engaged with the distal end of stent 52.

Release mechanism systems are shown in each of FIGS. 6 and 7. In the release mechanism system shown in FIG. 6, a metal wire, elongated loop 61 extends through lumen 62, the proximal end of loop 61 being engaged by a release mechanism such as release member 58. The distal end 61a of loop 61 extends to, or slightly through, the distal portion 63 of lumen 62. Flexible release wire 64 extends distally through release wire lumen 66, around the distal end of stent 67, and then proximally in a space 69 between inner tube 70 and outer tube 71. An end portion 65 of flexible release wire loops over both strands of elongated loop 61 in opening 68. Another portion of flexible return wire 64 extends through the strands of elongated loop 61 in opening 68. The proximal portion of flexible release wire 64 comprises one or more knots 73. When elongated loop 61 is pulled in the proximal direction, the end of flexible wire 64 looped over elongated loop 61 is released as the loop reaches opening 68, wherein the distal end 67 of the stent is released. As elongated loop 61 is pulled further proximally, the distal end 61a of elongated loop 61 engages flexible wire 64 and pulls it proximally as well through lumen 62. In this fashion the portion of flexible wire 64 that would otherwise be unrestrained and thus available to irritate a vessel lining or otherwise interfere with a procedure, would be contained within lumen 62.

An alternative release mechanism arrangement is shown in FIG. 7, where elongated loop 80 extends through lumen 81, which is interrupted by opening 82. A flexible wire 84 extends into opening 82 where it loops under and then over an end portion 85 of a stent. A proximal loop portion 86 of flexible wire 84 is looped under and engaged by elongated loop 80. A portion of flexible wire 84 passes within elongated loop 80. A distal portion 87 of flexible wire 84 is looped around the outer surface of catheter or tube 89 and forms knots 90. As elongated loop 80 is pulled proximally, loop portion 86 is disengaged from elongated loop 80 and the stent end portion 85 will be released. However, as elongated loop 80 is pulled proximally further, distal loop 91 engages flexible wire 84 and pulls it proximally also.

In the embodiment of the invention set forth in FIG. 8, the respective distal and proximal ends of a stent 10 are restrained by a restraining means 31 comprising a band 32 a fixation member 33. Two ends of fixation member 33 are attached to band 32 and the loop side of fixation member 33 passes over the external lateral surface of the stent 10 and is held within release wire lumen 27 by one or more fixation wires 34. Fixation wire 34 is contained within release wire lumen 27 which is adjacent to one or other lumens of sheath member 2. It is within the scope of the invention that a fixation wire 34 may extend through each of two separate side lumens 27 and/or that three fixation wires 34 may extend through two or three separate side lumens 27, where either one fixation wire would extend through each of three separate release wire lumens 27 or one fixation wire 34 would extend through one release wire lumen 27 and two fixation wires 34 would extend through a second, release wire lumen 27.

Preferably fixation member 33 has a weld, solder, or glue member 36 that decreases the size of the opening within fixation member 33, to ensure that the ball 38 at the end of the stent 10 does not become caught in said opening after stent deployment within the body duct.

The restraining mechanism is shown somewhat more clearly in FIG. 9, which represents a close-up of the portion of FIG. 8 identified as section A.

It would be appreciated by one skilled in the art that loop 33 and band 32 could have various functional equivalents. Such equivalents are disclosed, for example, in co-pending, commonly assigned U.S. patent application Ser. No. 08/060, 937, filed May 10, 1993, incorporated herein by reference.

Cystoscope 1 may be assembled in several pieces. The cystoscopic delivery system sheath is designed to adapt to most optics companies such as Olympus, Storz, Wolf, and Circon. As each optics has a different attachment to the sheath and also a different length different adapters are supplied to be able to use the standard cystoscopic stent delivery system with all rigid cystoscopic companies.

The stent delivery systems described herein are intended to be useful for the stents shown as well as other expandable stents. The same delivery system can be applied to esophagoscopy and tracheobronchoscopy in which stent insertion is needed. Also, the same stent delivery system can be made flexible to adapt a flexible cystoscope or other optics through its lumen, or it may adapt only to a guidewire and be inserted under fluoroscopy or other non-invasive location means. A preferred stent, such as that shown here, is described in co-pending U.S. patent application Ser. No. 07/781,174, filed Oct. 31, 1991, incorporated herein by reference.

More specifically, the preferred stent comprises a spatial spiral (helix) wound of wire of a material tolerated by the human body and which, furthermore, is not corroded or otherwise attacked by body liquids. Such a material, also known as a physiologically or medically acceptable material, could be one or more of several materials known for this purpose. Especially useful here are metals such as stainless steel, gold-plated medical grade stainless steel, stainless steel coated with silicone, bicarbon, or polytetrafluoroethylene, such as TEFLON®, tantalum, titanium, superelastic alloy such as nickel-titanium (Ni-Ti) alloys (commercially available as Nitinol or Tinel), or bioabsorbable/biodegradable material. The wire typically has a diameter of from about 0.1 to 2 mm, preferably from about 0.15 to 0.60 mm. Also, a strip of ellipsoidal, rectangular, rectangular with step, or S-shape wire is suitable for stent production.

It is important that the winding of the stent be sufficiently tight that the outer surface of the stent is substantially continuous, thus preventing "leaking through" of the inner lining of a vessel or duct. However, in cases in which incorporation of the stent into the wall of a duct is preferred, space of about 0.1 to 2.0 mm will be left between the loops of the coil, as in most vascular stent applications.

The preferred stent useful herein has thickened regions at the distal and proximal ends of the stent. In the text above reference is made to "ball 38"; however, each ball 38 can be spherical or non-spherical, so long as the "ball" functions as described. For example, in the embodiment shown in FIGS. 8 and 9, the "ball 38" could merely be a non-spherical thickened area, such as an egg, cone, or tear-drop shape, or a functionally equivalent loop, hole, or hook, that would cooperate with loop 33 to restrain an end of the stent.

The outer diameter and length of the device will vary according to the intended use. For prostatic or urinary use, the outer diameter of the wound device will typically be from about 10 to 40 French (from about 3.3 to 13.3 mm), and the length of the device can vary from about 2 to 15 cm, preferably from about 4 to 12 cm. It is also within the scope of the invention that the device may comprise two spirals connected by a wire, the spirals and wire preferably being a continuous wire.

A special property of nickel-titanium alloy (Nitinol) is used for the production of the stent. Shape memory alloys can be strained up to ten times more than ordinary spring materials without being plastically deformed. Such a property would enable one to compress the stent to a very small diameter over the delivery catheter.

When a bioabsorbable material is used, the stent can function as a temporary stent with the advantage of no necessity to remove it after its placement. Choosing the correct composition of the absorbable biodegradable material, the time of the degradation can be predetermined depending on the different application. For example, an inoperable prostatic cancer patient with urinary obstruction can be treated with a three month time absorbable stent. In this case the stent will function as a bridge to prevent Foley catheter treatment of the time until the hormonal treatment will alleviate the urinary flow obstruction by prostatic shrinkage.

The same principle can be used for BPH patients starting "prostate shrinking medications" such as "Proscar" treatment. These patients are awaiting prostatic volume shrinkage, which may take six months. In this case the lifetime function of absorbable/biodegradable stents will be 3 to 8 months time within which time the medication's effect will alleviate the urinary obstruction.

Absorbable/biodegradable polymers do not have the same elasticity as nitinol, so that if the absorbable/biodegradable stent is being stressed for a long time, or to its plastic deformation, it will not spring back to its premounted large diameter configuration. One of the objects of the invention is to use a simple way to reduce the stent diameter so that it will still "remember" its large diameter once implanted and released from the delivery system. A relative motion system is disclosed in U.S. Pat. No. 5,246,445, which enables controlled stent release and expansion as well as easy and user-friendly loading on the delivery catheter. The relative motion enables the operator to load the absorbable/biodegradable stent on the catheter just before starting the procedure. This pre-insertion, short time loading increases the spring-back dramatically as well as minimizes the plastic deformation during procedure.

Another application of the invention is to open the prostatic urethral lumen to a very large diameter (30 to 40 mm diameter), resulting in divulsion of the prostatic commissure and shrinkage of prostatic tissue. This method results in openings of the prostatic lumen and freeing of the patient from the obstruction caused by the pressure of the gland. This method has an advantage over the balloon dilatation of the prostate in that it opens the prostatic urethra slowly over a long period (up to a few days) and in that the constant pressure on prostatic tissue caused pressure atrophy. This atrophy makes prostatic volume smaller—and by doing so allows good urinary flow through the prostatic urethra. (Balloon dilatation results only in divulsion of prostatic commissures.) This method cannot be applied in the balloon dilatation of the prostate because in this short time procedure there is only tearing of prostatic commissures but not atrophy and lessening of prostatic cells, such as occurs with slow prostatic dilatation.

In prostatic strictures or in urethral strictures near the external sphincter there is a high risk of stent migration in the first one to the bladder and in the second one towards the penile meatus. To overcome this another two parts are added to the stent, namely, another open wire and another short closed loop (1–2cm). The straight wire is for holding the stent in the external sphincter area which is the fixed strongest part of the urethra. A system like this exists in Prostacath, a prostatic stent, and also in urethral prostheses manufactured in France.

In both of these stents the wire is a straight wire which makes it less flexible and does not allow easy movements of both spirals, one at an angle to the other. This situation applies more constant pressure on the bulbar and prostatic urethra and may cause stent penetration into the urethral lumen as well as urethral perforation/fistula—which have been reported in literature.

Here, a half to one turn straight wire curve in the circumference of the stent, is used between the two coils, this allows more flexibility of the wire and more free movement of both the distal and proximal spring portions of the stent. Also it does not disturb passing instruments through the stent lumen as this loop wire goes in the "periphery" of the stent lumen.

In FIG. 1 reference is made to window 40, which window can be advantageous in positioning a stent according to the invention. For example, when a stent known as the PROSTACOIL is inserted into the opening to the urinary bladder, the scope is inserted with the scope held back from the outer sheath, until the operator sees the bladder ridge. Then, the operator releases the stent. Similarly, if a stent known as the UROCOIL were inserted, the operator would insert the scope with the stent until the sphincteric area is seen and position the stent, at which point that stent would be released.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A cystoscope delivery system for implanting a flexible, generally cylindrical, expandable stent, comprising:

a rigid sheath having distal and proximal ends, said sheath defining a central lumen and at least one secondary lumen extending therethrough and having two longitudinally displaced openings extending from a secondary lumen radially to the surface of the sheath, a cystoscope comprising a distal scope member and a proximal viewing head, the distal scope member extending distally through the central lumen and being removable therefrom, a flexible, expandable stent having discrete proximal and distal ends, said stent being positioned circumferentially around said sheath, at least one release wire positioned in and extending through said at least one secondary lumen, and two or three restraining means, two of which are positioned at said distal and proximal ends of the stent and each having a restraining member extending over a respective end of the stent, said at least one release wire extending through said openings to hold at least one end of the stent and thus to hold the stent in position, such that when said at least one release wire is pulled proximally, at least one end of the stent is released from the restraining member to permit the stent to expand.

2. The delivery system of claim 1, wherein the sheath can receive a flexible optics or cystoscope or a flexible endoscope.

3. The delivery system of claim 1, wherein each said restraining member becomes positioned within a secondary lumen after the stent is released.

4. The delivery system of claim 1, wherein the stent has a gap and the distal end of the sheath has a window intended to view through the gap in a stent.

5. The delivery system of claim 1, wherein the proximal end of the sheath comprises a release wire control mechanism and a fluid inlet.

6. The delivery system of claim 5, wherein the fluid inlet is in fluid communication with the central lumen, said at least one secondary lumen, or both.

7. The delivery system of claim 1, wherein there are two restraining means.

8. The delivery system of claim 1 for enabling the loading of a medical implant a short time prior to insertion into a mammalian body, wherein creep deformation of the medical implant is reduced and recovery of the medical implant to its original, unloaded shape is optimized.

9. The delivery system of claim 8, wherein the implantable device is a bioabsorbable or biodegradable stent.

10. A cystoscope delivery system for implanting a flexible, generally cylindrical, expandable stent, comprising:

an inner sheath having distal and proximal ends, said sheath defining a central lumen and at least one secondary lumen extending therethrough and having a longitudinally displaced opening extending from a secondary lumen radially to the surface of the distal end of the inner sheath, an outer sheath having proximal and distal ends, the outer sheath being rotatably positioned concentric to the inner sheath, the distal end of the outer sheath terminating proximal to the distal end of the inner sheath, the wall of the outer sheath defining a lumen for a release wire, and an opening extending from the lumen radially to the outer surface of the outer sheath, a rigid cystoscope comprising a distal scope member and a proximal viewing head, the distal scope member extending distally through the central lumen and being removable therefrom, a flexible, expandable stent having discrete proximal and distal ends, said stent being positioned circumferentially around the distal end of the inner sheath, a release wire positioned in and extending through said at least one secondary lumen of the inner sheath, a release wire extending through the release wire lumen in the outer sheath, and two restraining means positioned at said distal and proximal ends of the stent and each having a restraining member extending over said distal and proximal ends of the stent, said at least one release wire extending through said openings to hold at least one end of the stent and thus to hold the stent in position, such that when said at least one release wire is pulled proximally, said at least one end of the stent is released from the restraining member to permit the stent to expand, the inner and outer sheaths being capable of holding the stent in a less stressed condition and then, prior to use, the outer sheath being rotated to cause the stent to be stressed and to lower its profile.

11. The delivery system of claim 10, wherein the inner sheath can receive a flexible optics or cystoscope or a flexible endoscope.

12. The delivery system of claim 10, wherein each said restraining member becomes positioned within a secondary lumen or the release wire lumen after the stent is released.

13. The delivery system of claim 10, wherein the stent has a gap and the distal end of the inner sheath has a window intended to view through the gap in a stent.

14. The delivery system of claim 10, wherein the proximal end of the inner sheath comprises a release wire control mechanism and a fluid inlet.

15. The delivery system of claim 14, wherein the fluid inlet is in fluid communication with the central lumen, said at least one secondary lumen, or both.

16. The delivery system of claim 10, wherein the stent is non-metallic.

17. The delivery system of claim 16, wherein the stent is bioabsorbable or biodegradable.

* * * * *